United States Patent
Chapelle et al.

(10) Patent No.: US 12,220,280 B2
(45) Date of Patent: Feb. 11, 2025

(54) CARDIAC DEVICE

(71) Applicants: Institut National De Recherche En Informatique Et En Automatique (INRIA), LeChesnay (FR); Institut National De La Sante Et De La Recherche Medicale, Paris (FR)

(72) Inventors: Dominique Chapelle, LeChesnay (FR); Philippe Moireau, LeChesnay (FR); Mathieu Pernot, Paris (FR); Mickaël Tanter, Paris (FR)

(73) Assignees: Institut National De Recherche En Informatique Et En Automatique, LeChesnay (FR); Institut National De La Sante Et De La Recherche Medicale, Paris (FR)

( * ) Notice: Subject to any disclaimer, the term of this patent is extended or adjusted under 35 U.S.C. 154(b) by 265 days.

(21) Appl. No.: 17/632,128

(22) PCT Filed: Jul. 29, 2020

(86) PCT No.: PCT/FR2020/051396
§ 371 (c)(1),
(2) Date: Feb. 1, 2022

(87) PCT Pub. No.: WO2021/019186
PCT Pub. Date: Feb. 4, 2021

(65) Prior Publication Data
US 2022/0273268 A1 Sep. 1, 2022

(30) Foreign Application Priority Data
Aug. 1, 2019 (FR) ...................................... 1908859

(51) Int. Cl.
 A61B 8/00 (2006.01)
 A61B 8/08 (2006.01)
 G01S 7/52 (2006.01)
(52) U.S. Cl.
 CPC ............ *A61B 8/485* (2013.01); *A61B 8/0883* (2013.01); *A61B 8/5223* (2013.01); *A61B 8/543* (2013.01); *G01S 7/52042* (2013.01)
(58) Field of Classification Search
 CPC ..... A61B 8/0083; A61B 8/5223; A61B 8/485; G01S 7/52042
 See application file for complete search history.

(56) References Cited

U.S. PATENT DOCUMENTS 5,840,028 A 11/1998 Chubachi et al.
2003/0216646 A1* 11/2003 Angelsen ................. A61B 8/06
 600/437

(Continued)

FOREIGN PATENT DOCUMENTS

CN 114667101 A 6/2022
EP 4007528 A1 2/2021

(Continued)

OTHER PUBLICATIONS

International Search Report and Written Opinion received for International Patent Application No. PCT/FR2020/051396, mailed on Oct. 5, 2020, 20 pages including English translation.

(Continued)

*Primary Examiner* — Rajeev P Siripurapu
(74) *Attorney, Agent, or Firm* — David D. Brush; Westman, Champlin & Koehler, P.A.

(57) ABSTRACT

A cardiac device comprises a transmitter (10) arranged to transmit at least one wave, a probe (12) arranged to measure a shear wave caused by a wave coming from the transmitter (10), a detector (14) arranged to detect a systole phase in an (Continued)

electrocardiographic signal, and an estimator (16) arranged to determine, during at least one cardiac cycle, the propagation speed of a plurality of shear waves caused by the transmission of waves in several directions towards the heart of a patient, to determine using the detector (14) that which has a maximum propagation speed during the systole phase, and to derive an active cardiac stress response therefrom (160).

10 Claims, 2 Drawing Sheets

(56) References Cited

U.S. PATENT DOCUMENTS

| | | |
|---|---|---|
| 2013/0317361 A1 | 11/2013 | Tabaru et al. |
| 2016/0345938 A1 | 12/2016 | Tanter et al. |
| 2018/0064412 A1 | 3/2018 | Messas et al. |
| 2018/0150598 A1 | 5/2018 | Kohls et al. |
| 2019/0183344 A1 | 6/2019 | Gallippi et al. |
| 2020/0253490 A1 | 8/2020 | Chabiniok et al. |
| 2021/0219870 A1 | 7/2021 | Chapelle et al. |

FOREIGN PATENT DOCUMENTS

| | | |
|---|---|---|
| FR | 3099357 A1 | 2/2021 |
| JP | H105226 A | 1/1998 |
| JP | 2005-520592 A | 7/2005 |
| JP | 2017-504435 A | 2/2017 |
| JP | 2022-543248 A | 10/2022 |
| WO | 03/077766 A1 | 9/2003 |
| WO | 2012/105152 A1 | 8/2012 |
| WO | 2015/114232 A1 | 8/2015 |
| WO | 2017/197404 A1 | 11/2017 |
| WO | 2021/019186 A1 | 2/2021 |

OTHER PUBLICATIONS

International preliminary report on patentability received for International Patent Application No. PCT/FR2020/051396, mailed on Feb. 10, 2022, 15 pages including English translation.

Search Report received for Japanese Patent Application No. 2022-506681, mailed on Jan. 26, 2024, 15 pages including English translation.

Villemain, et al., "Myocardial Stiffness Evaluation Using Noninvasive Shear Wave Imaging in Healthy and Hypertrophic Cardiomyopathie Adults," JACC: Cardiovascular Imaging, 2019, pp. 1135-1145, vol. 12, No. 7.

Correia, et al., "3D Elastic Tensor Imaging in Weakly Transversely Isotrophic Soft Tissues," Physics in Medicine and Biology, Institute of Physics Publishing, 2018, pp. 1-14, vol. 63, No. 15.

Villemain, "Myocardial Stiffness Evaluation Using Noninvasive Shear Wave Imaging in Healthy and Hypertrophic Cardiomyopathie Adults—Appendix," JACC: Cardiovascular Imaging, 2019, pp. 1-4, vol. 12, No. 7.

Japanese Notice of Reasons for Refusal dated Mar. 5, 2024 for corresponding Japanese Application No. 2022-506681.

* cited by examiner

[Fig. 1]
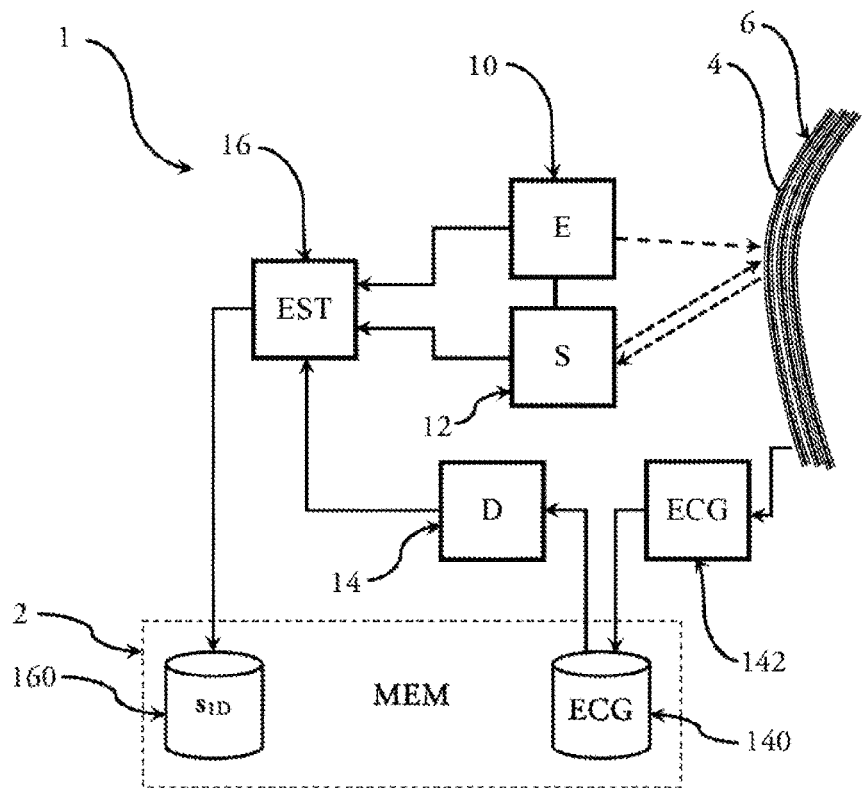
[Fig. 2]
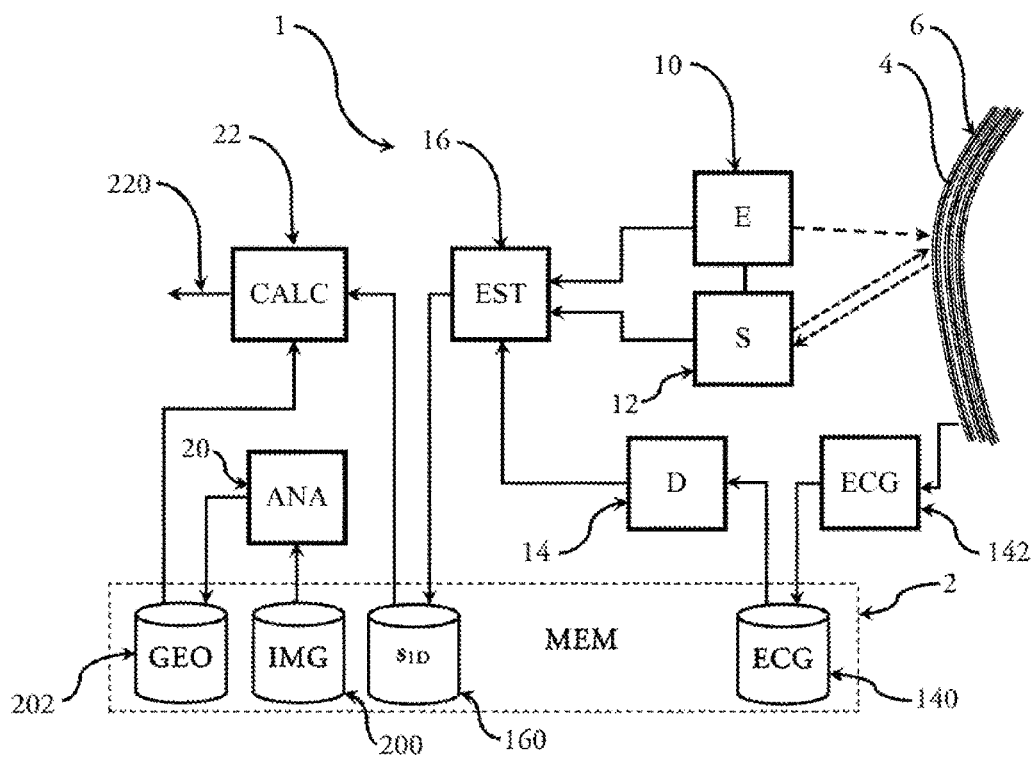

[Fig. 3]
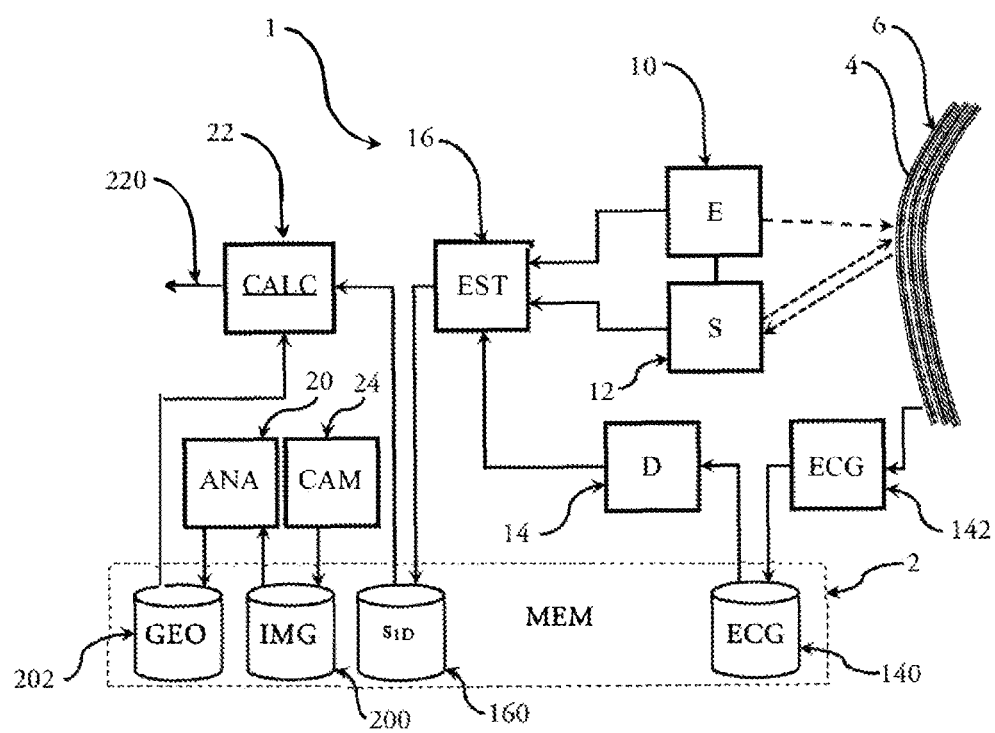

CARDIAC DEVICE

The present invention relates to the field of cardiac measurements, and more particularly to that of non-invasive cardiac measurements. Cardiac measurement encompasses measurements of physical parameters taken on the heart of a patient, in particular mechanical parameters.

Recent progress made in imaging, particularly ultrasound or magnetic resonance imaging, has made it possible to access parameters that were previously measured only by in situ methods. Such in situ methods involve accessing the heart through surgery or catheterisation. These methods are thus invasive and restrictive. Moreover, they can only be carried out in a suitable facility with strict regulations.

Opposingly, non-invasive measurements are easier to carry out. However, these measurements do not allow all useful or easily exploitable parameters to be measured. For example, a known method for obtaining radial blood pressure measurements uses sensors positioned close to the skin of a patient, for example via a wristband, finger sensor, or smart watch. However, the link between the radial blood pressure and the physical parameters within the heart, for example the central blood pressure, is imprecise and indirect.

Another known method involves measurements by magnetic resonance or ultrasound cardiac elastography. This technique is non-invasive and is used to measure the apparent stiffness of the heart tissue. The apparent stiffness is a parameter that varies during a heartbeat and depends on the point measured. This apparent stiffness could theoretically be linked to other useful cardiac parameters, such as the elastic modulus, heart pressure and tissue stress, etc. However, there is no direct relationship between this measurement and these cardiac parameters. Correlations have already been observed between the apparent stiffness and heart pressure, however they vary greatly from one individual to another.

There is thus no known method for non-invasively accessing useful cardiac parameters.

The invention improves this situation. For this purpose, the invention proposes a cardiac device comprising a transmitter arranged to transmit at least one wave, a probe arranged to measure a shear wave caused by a wave coming from the transmitter, a detector arranged to detect a systole phase in an electrocardiographic signal, and an estimator arranged to determine, during at least one cardiac cycle, the propagation velocity of a plurality of shear waves caused by the transmission of waves in several directions towards the heart of a patient, to determine, using the detector, that which has a maximum propagation velocity during the systole phase, and to derive an active cardiac stress therefrom.

This device is advantageous because it allows direct access to the active stress in the heart tissue. The active stress is a force per unit of area. This active stress allows direct and non-invasive access to a multitude of useful cardiac parameters. For example, the intraventricular pressure can be derived from the active stress. Cardiac pathologies can also be detected from an active stress measurement, allowing the after-effects of infarction to be observed for example.

In various alternative embodiments, the device can have one or more of the following features:
   the cardiac device comprises a calculator arranged to determine a ventricular pressure from a ventricular wall thickness, a ventricular cavity radius and the active stress determined by the estimator,
   the cardiac device comprises an image analyser arranged to determine the ventricular wall thickness and the ventricular cavity radius on the basis of at least one cardiac image,
   the at least one cardiac image is derived from shear wave imaging,
   the cardiac device further comprises an imager arranged to provide shear wave imaging from at least one shear wave measured by the probe,
   the at least one wave coming from the transmitter is compressional ultrasound,
   the transmitter and the probe are implemented by a two-dimensional echocardiography probe which has a probe direction defining a direction of propagation about which it can rotate, and wherein the estimator is arranged to determine the maximum propagation velocity on the basis of measurements carried out by the probe for three coplanar and non-collinear directions,
   the transmitter and the probe are implemented by a three-dimensional ultrasound probe,
   the three-dimensional ultrasound probe is a three-dimensional echocardiography probe.

Other features and advantages of the invention will be described in detail in the following description, which is given with reference to the accompanying drawings, in which:

FIG. 1 shows a diagrammatic view of the cardiac device according to the invention, FIG. 2 shows a diagrammatic view of the cardiac device of FIG. 1 in a configuration for measuring ventricular pressure, and FIG. 3 is a diagrammatic view of another configuration of the cardiac device in FIG. 2.

The accompanying drawings essentially contain elements of a definite nature. They can thus serve not only to assist with the understanding of the present invention, but also to contribute to the definition thereof, where appropriate.

The description is followed by an Annex A comprising mathematical formulae. This annex forms an integral part of the description.

Reference is now made to FIG. 1.

A cardiac device 1 according to the invention comprises a memory 2, a transmitter 10 and a probe 12.

The memory 2 can be any type of data storage suitable for receiving digital data: hard drive, solid state drive (SSD), flash drive of any form, random access memory, magnetic drive, cloud or local distributed storage, etc. The data stored in the memory 2 can be erased after the cardiac device 1 has carried out its tasks, or they can be saved. The data computed by the cardiac device can be stored in the memory 2 or in any type of memory similar thereto.

Techniques have been developed for the non-invasive observation of anisotropic (for example fibrous) media using ultrasound. For example, the patent application PCT/FR2015/050058 relates to the measurement of mechanical features within anisotropic media, by observing the propagation of ultrasound therein.

The transmitter 10 in this case is a device that is capable of transmitting ultrasound. An ultrasound transmitted by the transmitter 10 directed towards a fibrous tissue 4, for example the wall of a heart 6, causes, in reaction to it entering the fibrous tissue, a shear wave to propagate in this fibrous tissue in a plane orthogonal to the direction of transmission of the ultrasound. This propagation is observed by the probe 12 via compression ultrasound transmitted at a high rate, as described in the patent application PCT/FR2015/050058.

The cardiac device 1 further comprises a detector 14 and an estimator 16. The detector 14 determines the moments in time when the observed heart is in a systole phase, i.e. when the heart is contracting. The estimator 16 is connected to the transmitter 10, the probe 12 and the detector 14 so that it can receive data therefrom. The estimator 16 can derive one or more physical parameters from these data, in particular an active stress 160 of the heart tissue.

In order to carry out a propagation measurement, the transmitter 10 and the probe 12 are brought into contact with the skin of a patient whose heart 6 is to be observed, and directed towards the latter. The transmitter 10 and the probe 12 work together to observe the propagation of shear waves within heart tissue.

The transmitter 10 generates a focused ultrasound beam for a short period of time in a direction of transmission towards the heart 6. This beam, when it reaches the heart, causes the displacement of the heart tissue 4 under the effect of the acoustic radiation pressure. This displacement takes the form of a shear wave which propagates within the heart tissue 4 in a direction of propagation that is substantially orthogonal to the direction of transmission.

The probe 12 observes the propagation of the shear wave. For this purpose, the probe 12 transmits ultrasound in the form of compression waves at a high rate towards the heart 6. This ultrasound is reverberated by the heart tissue 4 deforming under the effect of the shear wave. The reverberated waves are detected by the probe 12, allowing the displacement of the heart tissue 4 to be observed. The probe 12 transmits ultrasound at a rate of greater than 300 Hz or even 500 Hz. Each individual shear wave propagation measurement can be carried out in about a few milliseconds. The probe 12 can thus observe the propagation of the shear wave within the heart tissue 4 with great accuracy and several hundred times per second. The probe 12 further determines the propagation velocity of the shear wave. The probe 12 can further associate the determined propagation velocity of the shear wave with the direction of propagation thereof.

In order to work together, the transmitter 10 and the probe 12 can be controlled by a user and/or by a controller. In the example described here, the transmitter 10 and the probe 12 are connected to one another in order to communicate with one another.

The Applicant has observed that the propagation velocity of a shear wave within fibrous heart tissue is maximal when this wave propagates in a direction tangent to the direction of the tissue fibres. Thus, by taking a plurality of propagation velocity measurements in different directions of propagation, the direction of the fibres in the fibrous tissue, and the propagation velocity of a shear wave along these fibres can be determined.

More specifically, the issue of determining the shear wave propagation along the fibres can be summarised in the form of the equation (1) in Annex A, which is also known as the Christoffel equation. In this equation, the first term is also known as the Christoffel matrix M, r is the density of the heart tissue, F is the polarisation vector of the wave, and V is the propagation velocity of the plane wave.

In the course of its works, the Applicant discovered that, during the systole phase, the active tension term dominates in the stress tensor of the fibrous cardiac medium. This allowed it to reformulate the Christoffel matrix M of the equation (1) into the general form of the equation (2) in Annex A, where $n_1$ is the cosine of the angle between the direction of propagation of the wave and the fibre direction, and where $s_{1D}$ is the active stress. In this equation, the matrix M is expressed in a frame of reference whose first vector is the fibre direction. By focusing on the fibre-transverse polarisation terms in the tensor (second and third term of the diagonal of the matrix M), which are equal to $s_{1D}*n_1^2$, and by feeding them back into the equation (1) in Annex A, the Applicant produced the equation (3) in Annex A. The Applicant then established the relationship between maximum propagation velocity, heart tissue density and active stress, expressed in the form of the equation (4) in Annex A, which corresponds to the case where $n_1$ is equal to 1.

The density r in this case is substantially equal to 1,060 kg/m$^3$. The density r shows little variability between individuals, since the proportion of water within the heart tissue is high. As a result, the Applicant's work can be used to measure the active stress in humans.

To determine the active stress 160, the systole phase must firstly be identified. For this purpose, the detector 14 determines a systole phase on the basis of an electrocardiographic signal 140. The electrocardiographic signal 140 in this case comes from an electrocardiograph 142 integrated into the cardiac device 1. Alternatively, the electrocardiographic signal 140 can originate from an appliance external to the cardiac device 1 and be stored in the memory 2. This alternative embodiment is not shown in the figures.

The systole phase lasts between 200 and 400 milliseconds. Given the duration of the measurement that can be carried out by the transmitter 10 and the probe 12, of the order of a few milliseconds, a large number of propagation velocity measurements can thus be carried out during a single systole phase.

The estimator 16 is, in this case, a program executed by the processor of a computer. Alternatively, it could be implemented in a different manner by means of a dedicated processor. The term 'processor' must be understood to mean any processor adapted to the data processing operations described herein. Such a processor can be produced in any known manner, in the form of a microprocessor for a personal computer, a dedicated chip of the FPGA or SoC (System on Chip) type, a computing resource on a grid, a microcontroller, or any other form suitable for providing the computing power required to carry out the operations described hereafter. One or more of these elements can also be produced in the form of specialised electronic circuits such as an ASIC. An electronic circuit-processor combination can also be considered.

The estimator 16 receives a set of propagation velocities determined by the probe 12, each propagation velocity being associated with the direction of propagation of the shear wave thereof. The estimator 16 receives information from the detector 14 indicating the systole phase. Based on the set of propagation velocities, the estimator 16 determines the maximum propagation velocity of the shear wave during the systole phase.

To do this, a user or an external controller controls the direction of transmission of the waves transmitted by the transmitter 10, such that a plurality of propagation velocity measurements can be carried out. From these, the estimator 16 determines the maximum propagation velocity of the shear wave within the heart tissue 4, i.e. the direction of the fibres of the heart tissue 4.

For this purpose, the estimator 16 can carry out a plurality of propagation velocity measurements in a plurality of directions of propagation distributed in the plane tangent to the heart wall, and take the largest of the measured propagation velocities. This plurality of directions of propagation can, for example, be chosen such that the angular distribution thereof is substantially even. The estimator 16 can further use the formula (3) to interpolate a sine wave from at least three propagation velocity measurements derived from coplanar and non-collinear directions of propagation of the waves transmitted by the transmitter 10, and derive the maximum propagation velocity of the shear wave within the heart tissue 4.

After determining the maximum propagation velocity, the estimator 16 derives therefrom the active stress 160, according to the formula (4) in Annex A.

In a first embodiment of the invention, the transmitter 10 and the probe 12 are implemented in a two-dimensional echocardiography probe. The ultrasound is transmitted by the transmitter 10 and focused into the heart tissue. The probe 12 transmits unfocused waves at a very high rate to image shear wave propagation in a plane. By rotating this plane substantially about this main probe axis, the ultrasound scans a cone or portion of a cone around this main probe axis. This thus allows a user to manually turn the two-dimensional echocardiography probe to obtain a plurality of propagation velocity measurements in at least three directions of propagation. The measurement of the directions of propagation can be manual, automated or guided. Thus, in a few seconds and via a simple handling operation, the maximum propagation velocity of the shear waves can be determined as described hereinabove. The ability to use a transmitter 10 and probe 12 in a two-dimensional echocardiography probe is highly advantageous, since these probes are inexpensive and available in most medical facilities. More generally, in this embodiment, the entire cardiac device 1 can be implemented in a conventional two-dimensional echocardiography device.

In a second embodiment, the transmitter 10 and the probe 12 are implemented in a three-dimensional echocardiography probe. In this configuration, the transmitter 10 transmits ultrasound in a plurality of directions of propagation, scanning a non-zero solid angle, for example a cone around a main probe axis. The measurement of the maximum propagation velocity is obtained in this case without the need to move or rotate the three-dimensional echocardiography probe. This makes the determination of the active stress more reliable, faster and more accurate. Furthermore, the cardiac device 1 in this case has the advantage that it can be implemented in a conventional three-dimensional echocardiography device.

In a third embodiment, the cardiac device 1 is implemented in a stand-alone appliance of the type described in the patent application PCT/FR2015/050058, which is different from an echocardiography device. This specialised device provides propagation measurements that are almost equivalent to those provided by a three-dimensional echocardiography probe, while being simpler in design and less expensive. The transmitter 10 and the probe 12 are arranged to carry out the maximum propagation velocity measurement without the need to move or rotate the stand-alone appliance. The portion of the stand-alone appliance containing the transmitter 10 and the probe 12 can be less than an intercostal distance in size. This small size increases the accuracy of the measurements carried out by the probe 12. The implementation of the cardiac device 1 in a stand-alone appliance of this type simplifies the manufacture thereof. Furthermore, in this configuration, the cardiac device 1 can be interfaced with a separate conventional medical appliance, to which it can transmit data, in particular a determined active stress 160.

Reference is now made to FIG. 2.

The Applicant has discovered a way to determine a ventricular pressure from the active cardiac stress. For this purpose, the Applicant has modelled the mechanical behaviour in static equilibrium of a substantially spherical ventricular cavity of thickness d and radius R. Under a pressure p, where e=d/R, the Applicant has produced the formula (5) in Annex A. This formula (5) relates the active stress 160, the thickness d and the radius R to the internal pressure 220, where $a_{cor}$ is a correction factor. The thickness d and the radius R are geometric data of the ventricular cavity.

In the embodiment described here, the cardiac device 1 comprises a calculator 22. The calculator 22 receives the active stress 160 from the estimator 16 and the geometric data 202. The calculator 22 determines a ventricular pressure using the formula (5) in Annex A, based on the active stress 160 and the geometric data 202.

The cardiac device 1 can optionally comprise an image analyser 20 for generating the geometric data 202.

The image analyser 20 retrieves image data 200 from the ventricular cavity of the observed heart. The image analyser 20 derives the geometric data 202 of the ventricular cavity therefrom. The image analyser 20 determines at least a ventricular wall thickness d and a ventricular cavity radius R of the ventricular cavity.

The image data 200 can come from a cardiac imaging method using ultrasound (echocardiography), magnetic resonance imaging (MRI), computed tomography (CT), radioactivity (nuclear medicine) or any other non-invasive cardiac imaging method. The image data can be stored in the memory 2. In the example described here, the image data 200 come from a third-party appliance.

The geometric data 202, and the image data 200 where appropriate, are stored in the memory 2.

In the first (respectively the second) embodiment, the image analyser 20 is connected to the two-dimensional (respectively the three-dimensional) echocardiography probe, and the latter provides the necessary image data to the image analyser 20. In the third embodiment, the cardiac device 1 also provides the necessary image data to the image analyser 20. The image analyser 20 can analyse the image data with a machine learning method or via an algorithm. The image analyser 20 can, for example, comprise a neural network, in particular a convolutional neural network, in order to recognise a shape within the image data, from which it can derive the geometric data.

The measurement of the ventricular wall thickness d and of the ventricular cavity radius R can be carried out using an echocardiographic image of the heart by determining the contour of the inner wall (endocardium) and outer wall (epicardium) of the heart. The segmentation in this case can be manual or automatic.

Alternatively, an image from a time-motion (TM) echocardiography probe representing an echographic line as a function of time can be obtained. This image gives a visualisation of the heart walls, which can then be manually or automatically segmented, in order to calculate the ventricular wall thickness d and the ventricular cavity radius R.

Given the spherical approximation of the ventricular cavity, the formula (5) comprises a correction factor $a_{cor}$. This correction factor can be determined in advance, for example by digital simulation, or measured for a group of patients. Alternatively, this correction factor can be determined on the fly by a component of the cardiac device 1 capable of geometric shape analysis or image analysis. This analysis, for example, could be carried out by the image analyser 20 from the image data 200. In the example described here, the correction factor can vary between 0.6 and 1, preferably between 0.75 and 0.95, and even more preferably it can be set at 0.9. The Applicant has estimated the variability of the correction factor between individuals to be approximately 10%. This variability is much less than that of known non-invasive pressure measurements. The use of the calculator 22 and the image analyser 20 thus procures a non-invasive measurement of the ventricular pressure 220 that is significantly more accurate than the conventional methods.

The non-invasive measurement of the ventricular pressure p by the cardiac device 1 allows multiple pathologies to be diagnosed using inexpensive equipment through a simple medical procedure. For example, heart failure could be detected by measuring the ventricular pressure using a cardiac device 1 implemented in a two-dimensional echocardiography probe. This non-invasive pressure measurement can also be used in cardiac resynchronisation therapy.

The image analyser 20 and the calculator 22 are programs that are executed by one or more processors of a computer. Alternatively, they could be implemented in a different way using dedicated processors, or on separate machines.

Reference is now made to FIG. 3.

In this embodiment, the cardiac device 1 comprises an imager 24 for generating the image data. When the cardiac device 1 is implemented in an echocardiography device, the imager 24 comprises the parts of the echocardiography device that carry out one or more echocardiographies.

The use of active stress to measure a ventricular pressure has been described. The after-effects of infarction can also be observed from the contractility, i.e. the maximum value of the active stress. This contractility measurement can be carried out over a full systolic cycle. Lower than normal contractility thus indicates an area that has been affected by an infarction.

ANNEX A

[Math. 1]

$$(1)\ M.F - r.V^2 F = 0$$

$$(2)\ \begin{pmatrix} s_{1D}*n_1^2 + C^{(2)} & 0 & 0 \\ 0 & s_{1D}*n_1^2 & 0 \\ 0 & 0 & s_{1D}*n_1^2 \end{pmatrix}$$

$$(3)\ V = n_1.(s_{1D}/r)^{1/2}$$

$$(4)\ s_{1D} = r.V^2$$

$$(5)\ p = a_{cor}.c.s_{1D}$$

The invention claimed is:

1. A cardiac device comprising:
a transmitter arranged to transmit at least one transmission wave;
a probe arranged to measure a plurality of shear waves caused by the at least one transmission wave;
a detector arranged to detect a systole phase in an electrocardiographic signal; and
at least one a processor configured to determine, during at least one cardiac cycle, a propagation velocity of the plurality of shear waves caused by the at least one transmission wave in several directions towards a heart of a patient, to determine, among said plurality of shear waves and using the detector, a shear wave which has a maximum propagation velocity during the systole phase, and to derive an active cardiac stress from said maximum propagation velocity.

2. The cardiac device according to claim 1, wherein said at least one processor is further configured to determine a ventricular pressure from a ventricular wall thickness, a ventricular cavity radius and the active stress determined by said at least one processor.

3. The cardiac device according to claim 2, wherein said at least one processor is further configured to determine the ventricular wall thickness and the ventricular cavity radius on the basis of at least one cardiac image.

4. The cardiac device according to claim 3, wherein said at least one processor is further configured to determine the ventricular wall thickness and the ventricular cavity radius on the basis of at least one cardiac image derived from shear wave imaging.

5. The cardiac device according to claim 4, wherein said at least one processor is further configured provide shear wave imaging from at least one of the plurality of shear waves measured by the probe.

6. The cardiac device according to claim 1, wherein the at least one transmission wave coming from the transmitter is compressional ultrasound.

7. The cardiac device according to claim 1, wherein the transmitter and the probe are comprises by a two-dimensional echocardiography probe which has a probe direction defining a direction of propagation about which the probe can rotate, and wherein the at least one processor is further configured to determine the maximum propagation velocity on the basis of measurements carried out by the probe for three coplanar and non-collinear directions.

8. The cardiac device according to claim 1, wherein the transmitter and the probe are comprises by a three-dimensional ultrasound probe.

9. The cardiac device according to claim 8, wherein the three-dimensional ultrasound probe is a three-dimensional echocardiography probe.

10. A method comprising:
transmitting at least one transmission wave in several directions from a transmitter towards a heart of a patient, the at least one transmission wave causing a plurality of shear waves to propagate from the heart;
measuring the plurality of shear waves with a probe;
detecting a systole phase in an electrocardiographic signal using a detector; and
using at least one a processor to determine, during at least one cardiac cycle, a propagation velocity of the plurality of shear waves caused by the at least one transmission wave in the several directions, to determine, among said plurality of shear waves and using data from the detector, a shear wave which has a maximum propagation velocity during the systole phase, and to derive an active cardiac stress from said maximum propagation velocity.

\* \* \* \* \*